United States Patent
Zhu et al.

(10) Patent No.: US 8,135,113 B2
(45) Date of Patent: Mar. 13, 2012

(54) IMAGE CAPTURE SYSTEM FOR RECORDING X-RAY IMAGES IN REAL TIME

(75) Inventors: Hong-Yu Zhu, Taoyuan (TW);
Ming-Chang Wu, Taoyuan (TW);
Chi-Bin Wu, Taoyuan (TW)

(73) Assignee: AccuMIS Inc., Taipei County (TW)

( * ) Notice: Subject to any disclaimer, the term of this patent is extended or adjusted under 35 U.S.C. 154(b) by 305 days.

(21) Appl. No.: 12/652,754

(22) Filed: Jan. 6, 2010

(65) Prior Publication Data
US 2011/0075803 A1   Mar. 31, 2011

(30) Foreign Application Priority Data
Sep. 25, 2009 (TW) ............................... 98132604 A

(51) Int. Cl.
*H05G 1/56* (2006.01)
*H05G 1/30* (2006.01)
*H05G 1/60* (2006.01)
*H05G 1/08* (2006.01)

(52) U.S. Cl. ............ 378/91; 378/42; 378/114; 378/189; 378/190; 600/425; 600/429

(58) Field of Classification Search ............ 378/42, 378/91, 98.8, 114, 189, 190; 600/407, 425, 600/429
See application file for complete search history.

(56) References Cited

U.S. PATENT DOCUMENTS

| | | | |
|---|---|---|---|
| 6,285,902 B1 * | 9/2001 | Kienzle et al. | 600/427 |
| 6,470,207 B1 * | 10/2002 | Simon et al. | 600/426 |
| 6,491,429 B1 * | 12/2002 | Suhm | 378/205 |
| 6,496,558 B2 * | 12/2002 | Graumann | 378/39 |
| 6,527,443 B1 * | 3/2003 | Vilsmeier et al. | 378/205 |
| 6,533,455 B2 * | 3/2003 | Graumann et al. | 378/205 |
| 6,823,207 B1 * | 11/2004 | Jensen et al. | 600/427 |
| 6,851,855 B2 * | 2/2005 | Mitschke et al. | 378/207 |
| 6,895,268 B1 * | 5/2005 | Rahn et al. | 600/429 |
| 6,932,506 B2 * | 8/2005 | Mitschke et al. | 378/207 |
| 7,010,095 B2 * | 3/2006 | Mitschke et al. | 378/162 |
| 7,340,291 B2 * | 3/2008 | Graumann et al. | 600/427 |
| 7,835,557 B2 * | 11/2010 | Kendrick et al. | 382/128 |

\* cited by examiner

*Primary Examiner* — Allen C. Ho
(74) *Attorney, Agent, or Firm* — Stites & Harbison, PLLC; Juan Carlos A. Marquez, Esq

(57) ABSTRACT

An image capture system for recording X-ray images in real time is disclosed. The image capture system includes an image pickup device, a sensing module and a surgical navigation device. The sensing module is used to detect the on/off status of the image pickup device. While the image pickup device is turned on to capture an X-ray image, the sensing module transmits a notification signal to the surgical navigation device. After receiving the notification signal, the surgical navigation device records the X-ray image captured by the image pickup device and the relative position between the image pickup device and the patient in real time. Thus, the real-time recording of the relative position between the image pickup device and the patient will prevent inaccurate image reading that occurs when the patient's position and image pickup device shift after the X-ray image has been captured.

8 Claims, 7 Drawing Sheets

IMAGE CAPTURE SYSTEM FOR RECORDING X-RAY IMAGES IN REAL TIME

BACKGROUND OF THE INVENTION

1. Technical Field

The present invention relates to an image capture system for recording X-ray images in real time. More particularly, it relates to an image capture system for recording X-ray images in real time and is applicable to a surgical navigation system.

2. Description of Related Art

Conventionally, prior to orthopaedic surgery, medical imaging instruments, such as CT (Computed Tomography) scanners, MRI (Magnetic Resonance Imaging) devices, etc., are used to capture images of patients' nidi for giving doctors more information about the locations and sizes of nidi. Consequently, doctors can plan incision locations, directions, depths, and the like according the images. However, even by reading such images, the doctors have to conjecture nidus locations with their knowledge of the anatomy or from their clinical experience. Accurate pre-surgery planning is difficult to accomplish in practice, especially in cases where the nidi is nestled deep inside the body. As a result, doctors are put in the predicament where they are forced to cut through layers of tissue, blindly seeking for the nidi.

For eliminating such predicaments, a doctor may implement a surgical navigation system to obtain pictures of nidi before surgical operation and employ image analysis software to reconstruct the pictures into three-dimensional images. Then the three-dimensional images can be read and accurate pre-surgery planning can be achieved by using the same so as to render subsequent surgery less difficult and more successful. However, in addition to clear, high-definition images, accurate pre-surgery planning and smooth surgical operation also require highly precise information about the relative position between the images and the patient's actual nidus.

Generally speaking, for such a surgical navigation system to precisely guide a surgical instrument to a nidus during operation, position marks may be provided to an X-ray machine and the nidus so that after X-ray images of the patient's nidus are taken, the surgical navigation system can show the relative position between the X-ray machine and the patient's nidus, thereby obtaining image coordinates of the nidus.

FIG. 1A is a schematic drawing showing usage of a conventional surgical navigation device 10 and an X-ray machine 11 while FIG. 1B is another schematic drawing of the surgical navigation device 10 and the X-ray machine 11.

As shown in FIG. 1A, a typical surgical navigation device 10 uses an image capture device therein to obtain X-ray images from a display device of the X-ray machine 11 or from the X-ray machine 11 itself. A position device 12 in the surgical navigation device 10 records the relative relation between the X-ray images (i.e. the position of the X-ray machine 11) and a nidus. However, since the X-ray machine 11 commonly implemented in hospitals is not linked to the surgical navigation device 10, and a shutter button of the X-ray machine 11 and an image-taking switch of the surgical navigation device 10 are provided separately at the two individual apparatuses. During operation, an operator has to first trigger the shutter button of the X-ray machine 11 in order to take the X-ray images, turn on the image-taking switch of the surgical navigation device 10 to acquire the X-ray images, and finally, actuate the position device 12 of the surgical navigation device 10 so as to derive the relative position between the X-ray machine 11 and the nidus.

Nevertheless, as shown in FIG. 1B, after the X-ray images are taken, once the patient unintentionally moves and causes change in the relative position between the nidus and the X-ray machine 11, the relative relation between the X-ray machine 11 and the nidus determined by the surgical navigation device 10 becomes untrue. As a result, the surgical navigation device 10 may erroneously guide the surgical instrument and thus the accuracy of the surgical navigation is compromised.

SUMMARY OF THE INVENTION

The present invention thus provides an image capture system for recording X-ray images in real time. By sensing movements from an image pickup device, the image capture system records X-ray images and the relative position between the image pickup device and the patient in real time, thus improving the accuracy in surgical operations.

The present invention also provides an image capture system for recording X-ray images in real time. The image capture system, by recording the relative position between the image pickup device and the patient in real time and acquiring correct image coordinates, is unlikely to acquire an inaccurate relative position.

To achieve the above effects, the image capture system for recording X-ray images in real time of the present invention includes: an image pickup device having: an image acquisition unit that uses an X-ray to take X-ray images; and a switch unit configured to turn on/off the image acquisition unit so as to power the image pickup device on or off; a sensing module having: a detection unit for detecting the on/off status of the image pickup device and for transmitting an actuating signal; and a signal transmission unit electrically connected with the detection unit for receiving the actuating signal and transmitting a notification signal; and a surgical navigation device having a signal reception unit for receiving notification signals so as to record the X-ray image in real time as well as the relative position between the image pickup device and the patient in real time.

By implementing the present invention, at least the following progressive effects can be achieved:

1. By sensing movements of the image pickup device, the X-ray images can be taken and the relative position between the image pickup device and the patient can be acquired in real time, thus improving the accuracy of surgical operations.

2. By using the sensing module to detect the image acquisition of the image pickup device, real-time recording of X-ray images and the accurate relative position between the image pickup device and a patient can be achieved, thereby preventing inaccurate guidance.

BRIEF DESCRIPTION OF THE DRAWINGS

The invention as well as a preferred mode of use, further objectives and advantages thereof will be best understood by reference to the following detailed description of illustrative embodiments when read in conjunction with the accompanying drawings, wherein.

DETAILED DESCRIPTION OF THE PREFERRED EMBODIMENTS

Figure 1A:
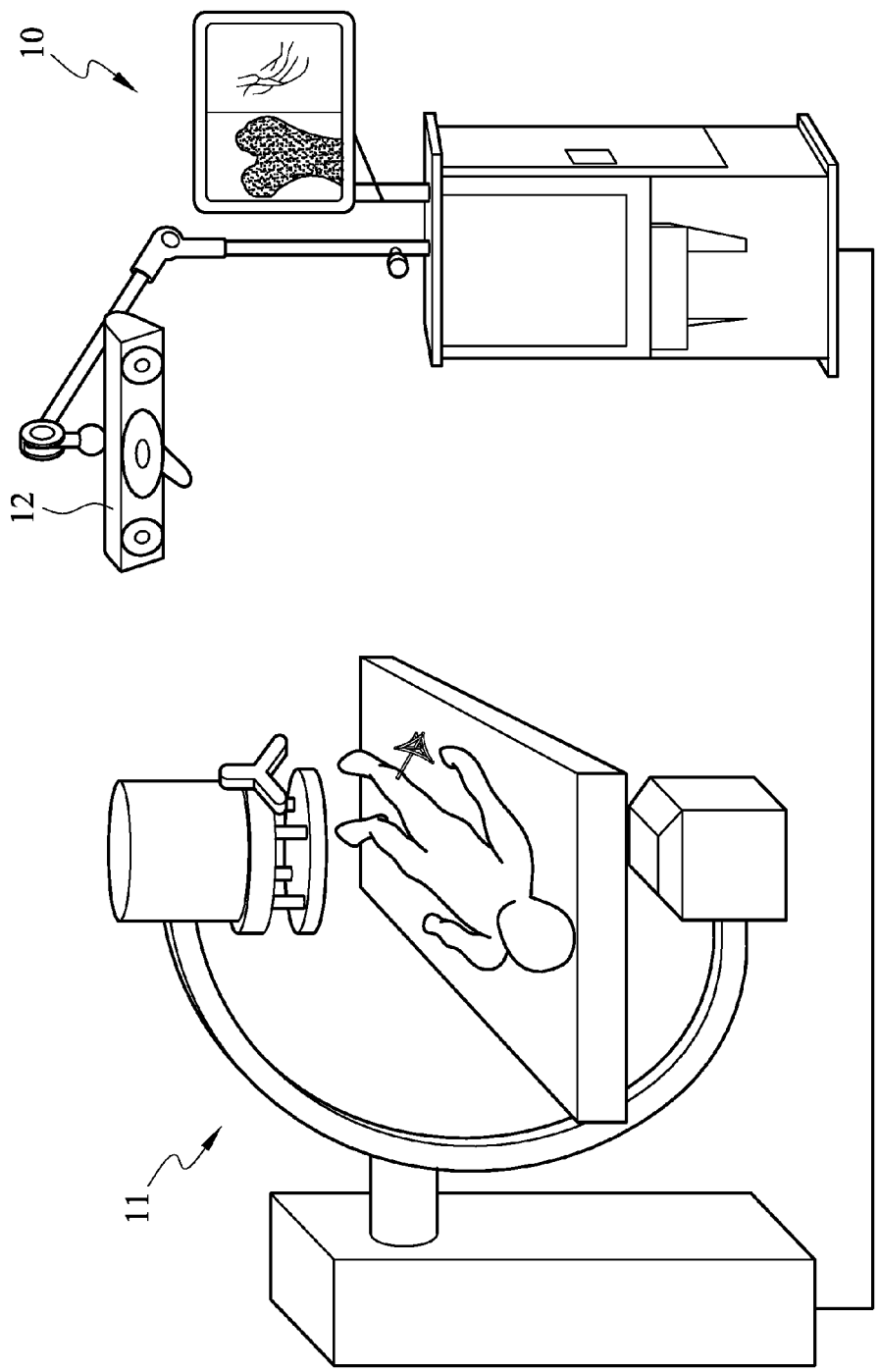
FIG. 1A is a schematic drawing of a conventional surgical navigation device and an X-ray machine.
Figure 1B:
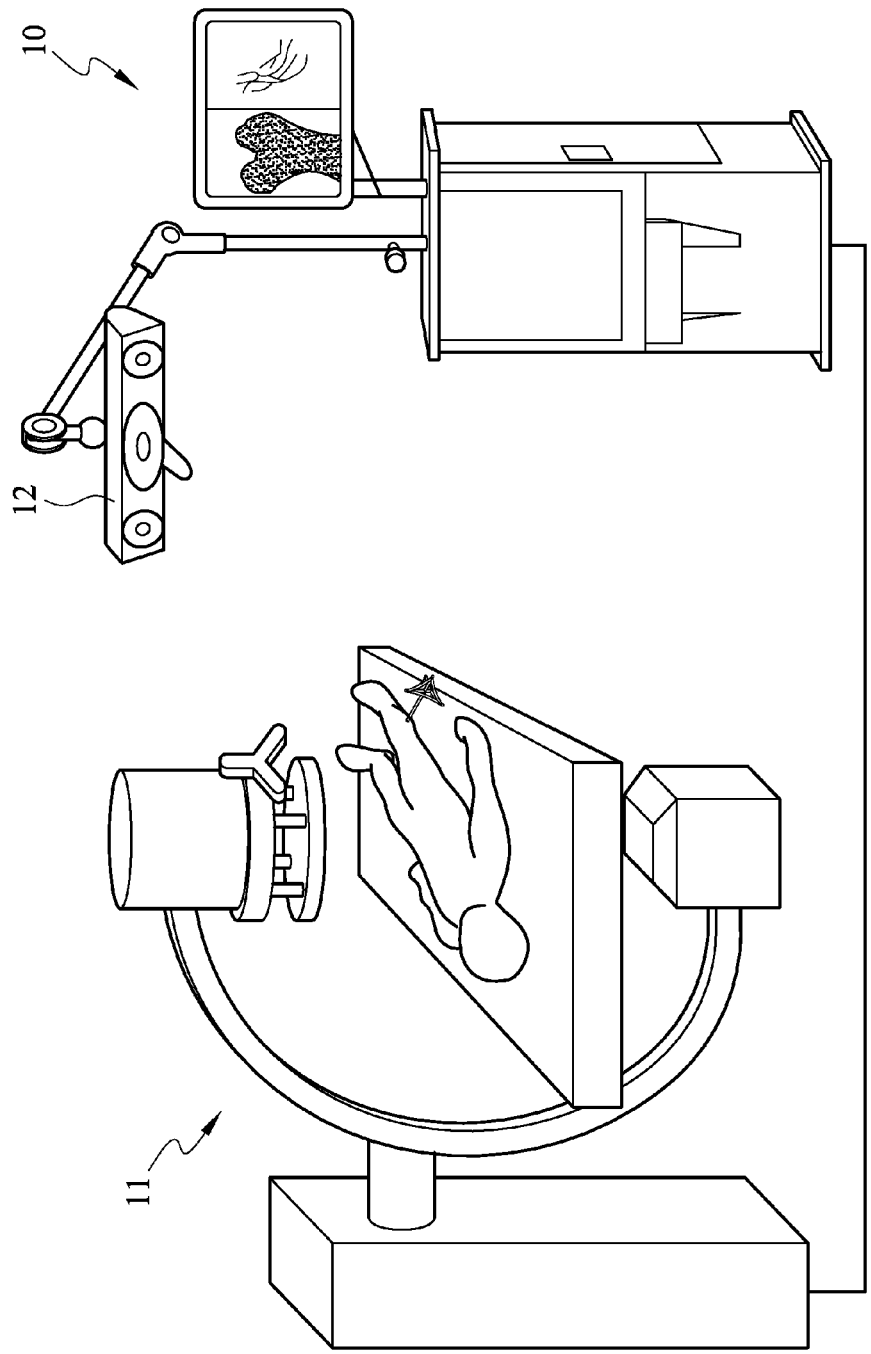
FIG. 1B is another schematic drawing of the conventional surgical navigation device and the X-ray machine.
Figure 2A:
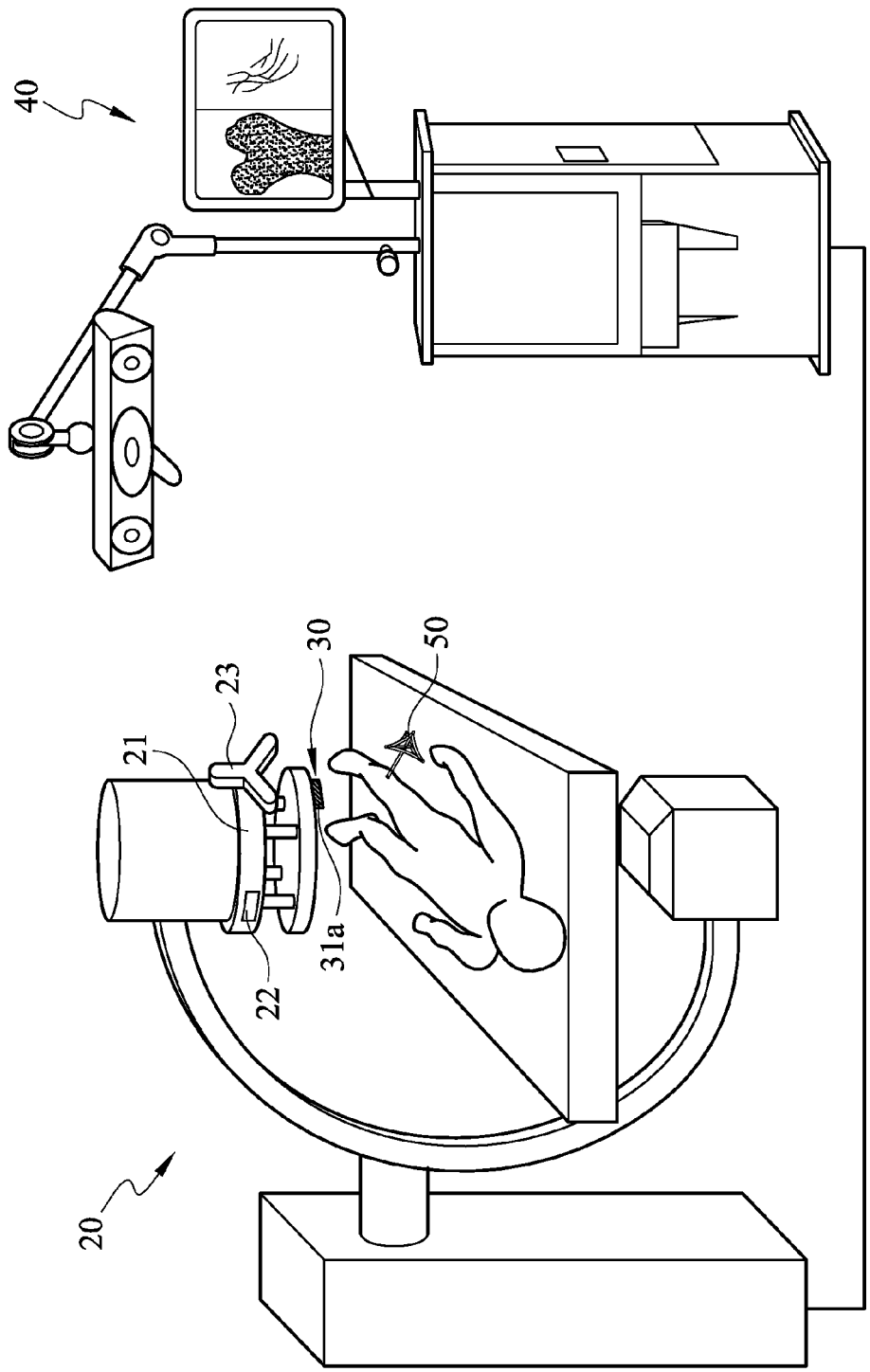
FIG. 2A shows a first concept of an image capture system for recording X-ray images in real time according to the present invention.

Referring to FIG. 2A, the present embodiment is an image capture system for recording X-ray images in real time. The image capture system includes: an image pickup device 20, a sensing module 30, and a surgical navigation device 40.

Figure 2B:
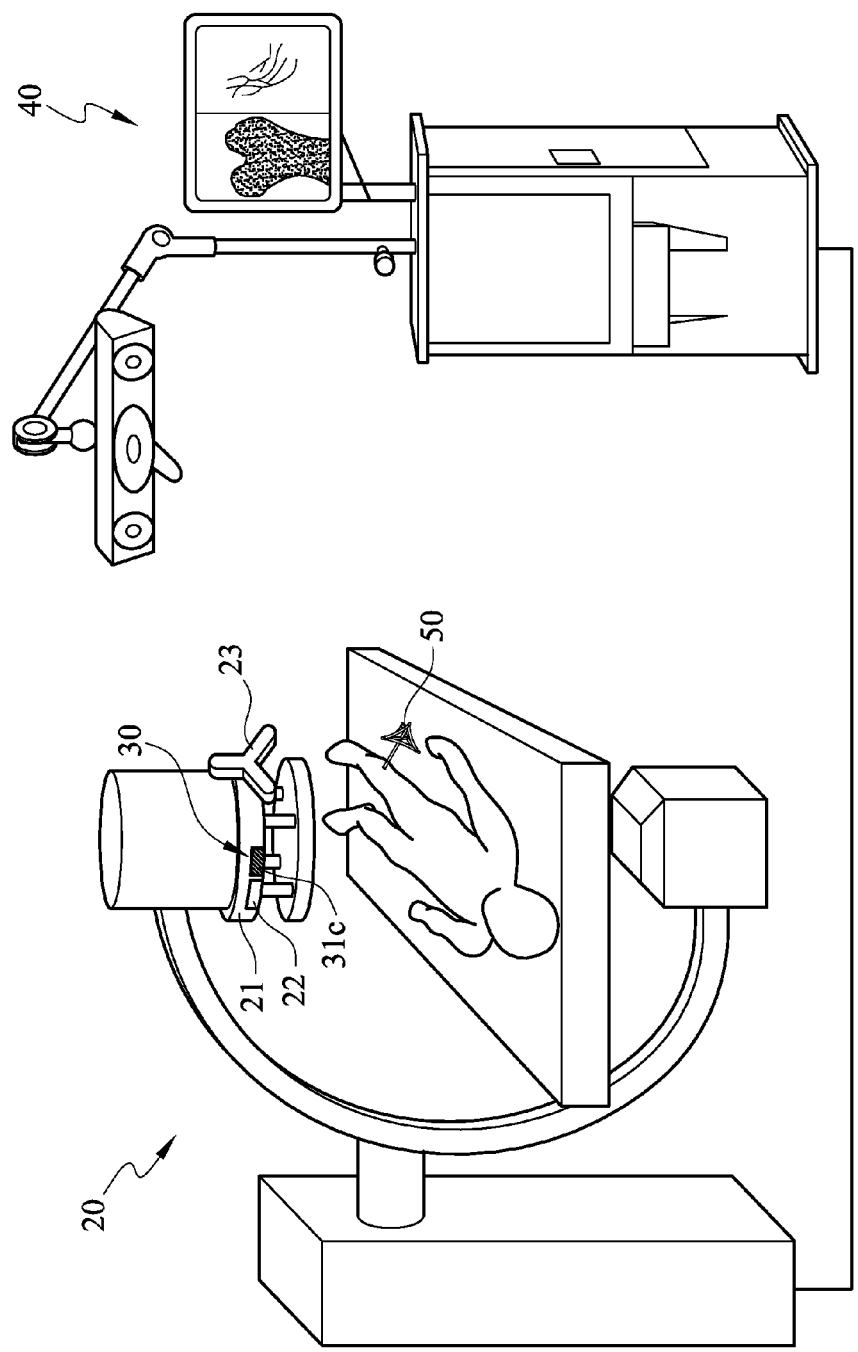
FIG. 2B shows a second concept of an image capture system for recording X-ray images in real time according to the present invention.

As shown in FIG. 2A and FIG. 2B, the image pickup device 20 may be an X-ray machine, an X-ray image calibrator, or a C-arm image capture device. The image pickup device 20 has an image acquisition unit 21 and a switch unit 22, wherein the image acquisition unit 21 uses an X ray to take X-ray images, while the switch unit 22 serves to turn on/turn off the image acquisition unit 21. Therefore, when a patient lies on an operating table, the switch unit 22 can be operated to control the image acquisition unit 21 to take X-ray images of a nidus of the patient, thus obtaining images of the nidus (as shown in FIG. 4A).

Still referring to FIG. 2A and FIG. 2B, for allowing the surgical navigation device 40 to recognize the position of the image pickup device 20, a shooting position mark 23 may be adjoined to the image acquisition unit 21, so as to facilitate the surgical navigation device 40 in obtaining spatial coordinates of the image pickup device 20. Moreover, an additional nidus position mark 50 is provided at the patient's nidus, so that the surgical navigation device 40 can acquire the spatial coordinates of the nidus.

Figure 4A:
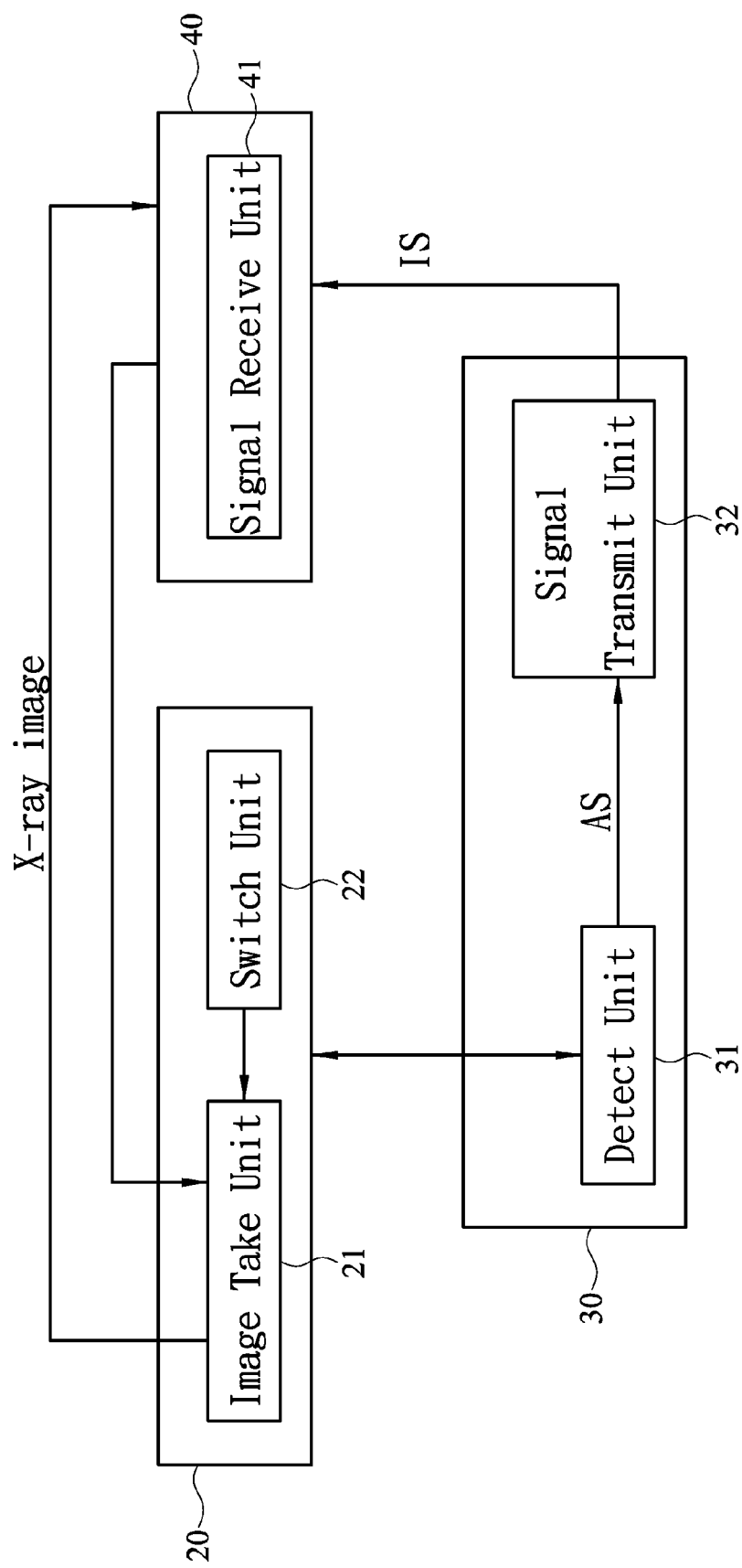
FIG. 4A is one illustrative circuit block diagram of the image capture system for recording X-ray images in real time according to the present invention.
Figure 4B:
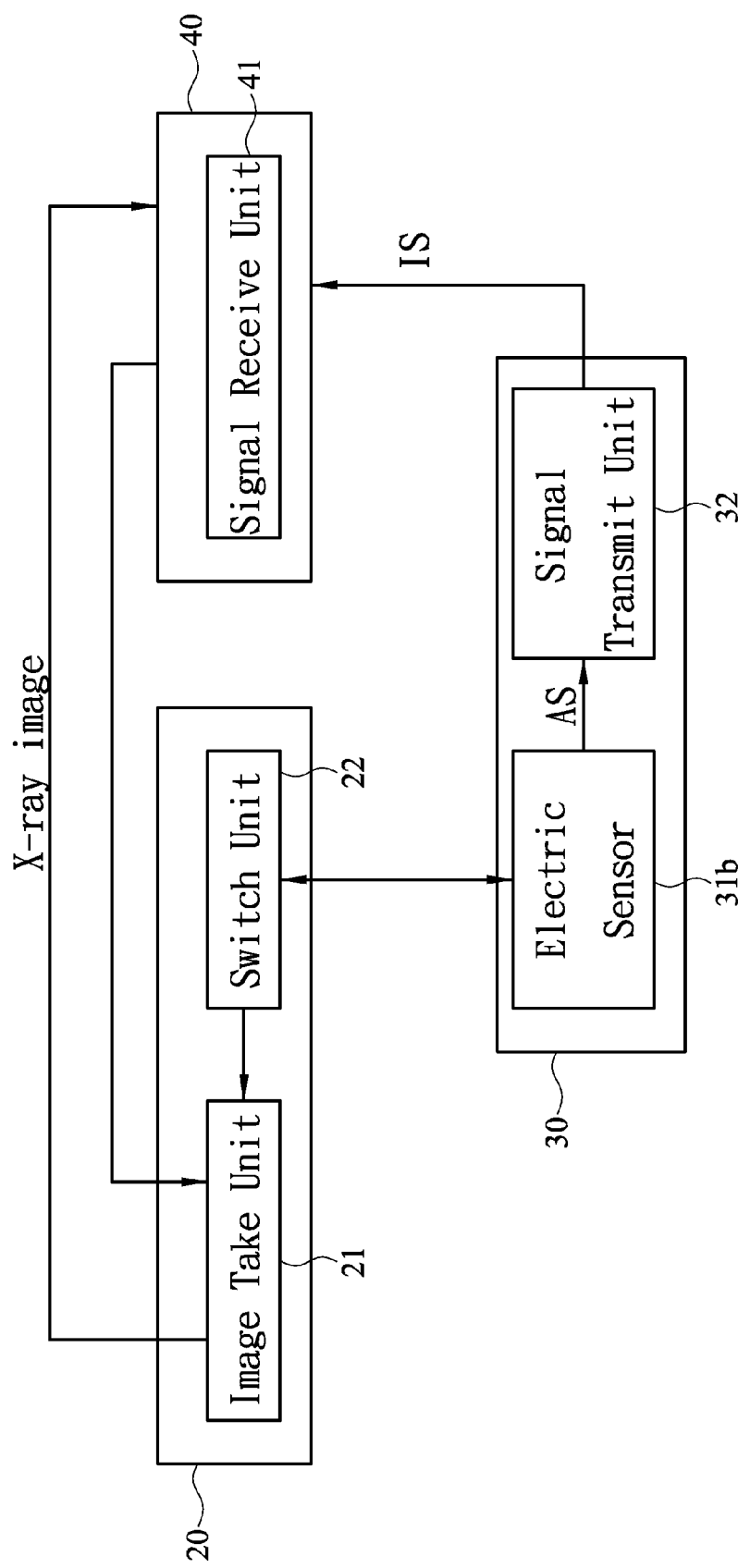
FIG. 4B is another illustrative circuit block diagram of the image capture system for recording X-ray images in real time according to the present invention.

As shown in FIG. 4A, the sensing module 30 has a detection unit 31 and a signal transmission unit 32. The signal transmission unit 32 is signally connected with the detection unit 31. Therein, the detection unit 31 may be a photonic sensor 31a, and the detection unit 31 may be arranged below the image acquisition unit 21 (as shown in FIG. 2A), for detecting whether the image pickup device 20 starts the X ray. Furthermore, the detection unit 31 may be an electric sensor 31b signally connected with the switch unit 22 (as shown in FIG. 4B), so that the electric sensor 31b is allowed to discern the on/off status of the switch unit 22.

Figure 3A:
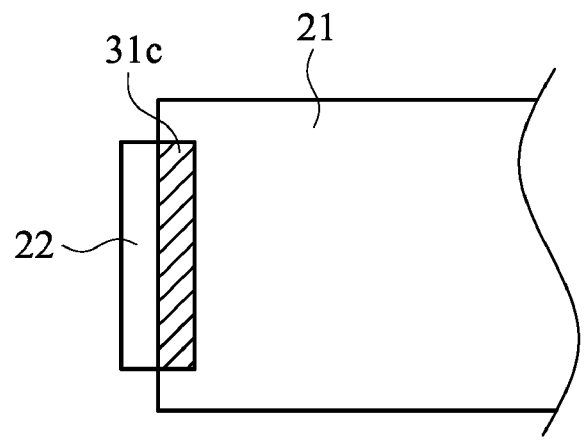
FIG. 3A is a first embodiment of combination between a detect unit and a switch unit according to the present invention.
Figure 3B:
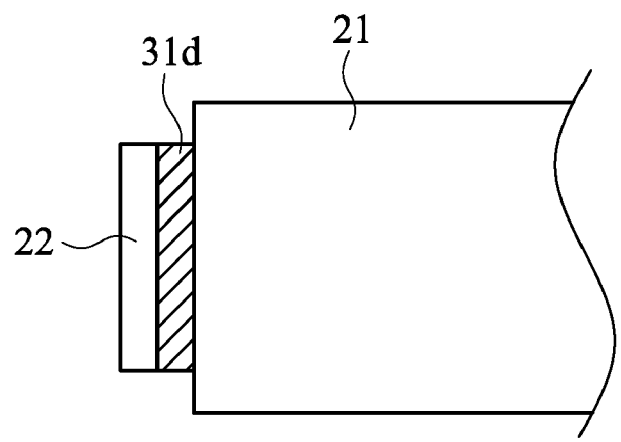
FIG. 3B is a second embodiment of combination between the detect unit and the switch unit according to the present invention.

Alternatively, the detection unit 31 may be a pressure sensor 31c, arranged at an outer side of the switch unit 22 (as shown in FIG. 2B) or below the switch unit 22 (as shown in FIG. 3A), for discerning the on/off status of the switch unit 22. Preferably, the detection unit 31 is a contact switch 31d attached to the switch unit 22 for discerning the on/off status of the switch unit 22 (as shown in FIG. 3B).

As shown in FIG. 4A, since the detection unit 31 is capable of detecting the on/off status of the image pickup device 20, when the detection unit 31 detects that the image pickup device 20 has been turned on, the detection unit 31 transmits an actuating signal AS to the signal transmission unit 32. The signal transmission unit 32, upon receiving the actuating signal AS, actively transmits a notification signal IS. The signal transmission unit 32 may be, but is not limited to, a wired transmission unit or a wireless transmission unit.

As shown in FIG. 4A, the surgical navigation device 40 has a signal reception unit 41 for receiving the notification signal IS output by the signal transmission unit 32. Moreover, the configuration of the signal reception unit 41 is subject to that of the signal transmission unit 32, which can be a wired reception unit or a wireless reception unit.

Upon receiving the notification signal IS output by the signal transmission unit 32, the surgical navigation device 40 actively and timely receives and records the X-ray images taken by the image acquisition unit 21. At the same time, the surgical navigational device 40 acquires the shooting position mark 23 on the image acquisition unit 21 and the nidus position mark 50 on the nidus. Therefore, one can calculate the imaging position of the image acquisition unit 21 corresponding with the nidus, thereby deriving the relative position between the image acquisition unit 21 and the nidus, and in turn, the image coordinates of the nidus. Consequently, the surgical navigation device 40 can guide a surgical instrument according to the image coordinates.

Because the correct image coordinates are acquired in real time, the problem related to asynchronous relative position between the image acquisition unit 21 and the patient's nidus caused by displacement of the patient can be solved, thereby improving the accuracy when the surgical navigation device 40 guides the surgical instrument.

The embodiments described above are intended only to demonstrate the technical concept and features of the present invention so as to enable a person skilled in the art to understand and implement the contents disclosed herein. It is understood that the disclosed embodiments are not to limit the scope of the present invention. Therefore, all equivalent changes or modifications based on the concept of the present invention should be encompassed by the appended claims.

What is claimed is:

1. An image capture system for recording X-ray images in real time, the image capture system comprising:
   an image pickup device having:
   an image acquisition unit that uses an X ray to take X-ray images; and
   a switch unit configured to turn on/off the image acquisition unit so as to power the image pickup device on or off;
   a sensing module having:
   a detection unit for detecting an on/off status of the image pickup device and for transmitting an actuating signal; and
   a signal transmission unit electrically connected with the detection unit for receiving the actuating signal and transmitting a notification signal; and
   a surgical navigation device having a signal reception unit for receiving the notification signal to record the X-ray image in real time as well as a relative position between the image pickup device and the patient in real time.

2. The image capture system of claim 1, wherein the image pickup device is an X-ray machine or an X-ray image calibrator.

3. The image capture system of claim 1, wherein the detection unit is a photonic sensor for detecting actuation of the X-ray.

4. The image capture system of claim 1, wherein the detection unit is an electric sensor that detects the on/off status of the image pickup device by discerning the on/off status of the switch unit.

5. The image capture system of claim 1, wherein the detection unit is a pressure sensor that detects the on/off status of the image pickup device by discerning the on/off status of the switch unit.

6. The image capture system of claim 1, wherein the detection unit is a contact switch, and attached to the switch unit that detects the on/off status of the image pickup device by discerning the on/off status of the switch unit.

7. The image capture system of claim 1, wherein the signal transmission unit is a wired transmission unit or a wireless transmission unit.

8. The image capture system of claim 1, wherein the signal reception unit is a wired reception unit or a wireless reception unit.

* * * * *